(12) United States Patent
Abdul-Karim

(10) Patent No.: US 10,179,009 B2
(45) Date of Patent: Jan. 15, 2019

(54) NEEDLELESS TRANSSEPTAL ACCESS DEVICE AND METHODS

(76) Inventor: Ahmad Abdul-Karim, Oak Brook, IL (US)

( * ) Notice: Subject to any disclaimer, the term of this patent is extended or adjusted under 35 U.S.C. 154(b) by 732 days.

(21) Appl. No.: 13/568,504

(22) Filed: Aug. 7, 2012

(65) Prior Publication Data

US 2014/0046356 A1 Feb. 13, 2014

(51) Int. Cl.
*A61B 17/00* (2006.01)
*A61B 17/34* (2006.01)
*A61B 17/32* (2006.01)
*A61B 17/22* (2006.01)

(52) U.S. Cl.
CPC .... *A61B 17/3478* (2013.01); *A61B 17/32002* (2013.01); *A61B 2017/00247* (2013.01); *A61B 2017/22044* (2013.01)

(58) Field of Classification Search
CPC .................. A61C 1/18; A61B 17/1631; A61B 17/320016; A61B 17/1622; A61B 17/3478; A61B 17/32002; A61B 2017/22044; A61B 2017/00247
See application file for complete search history.

(56) References Cited

U.S. PATENT DOCUMENTS

| | | | |
|---|---|---|---|
| 4,919,146 A | | 4/1990 | Rhinehart et al. |
| 5,041,082 A | * | 8/1991 | Shiber ............................. 604/22 |
| 5,047,040 A | | 9/1991 | Simpson et al. |
| 5,330,496 A | * | 7/1994 | Alferness ............. A61B 5/0422 606/171 |
| 5,366,468 A | | 11/1994 | Fucci et al. |
| 5,423,824 A | | 6/1995 | Akerfeldt et al. |
| 5,649,941 A | | 7/1997 | Lary |
| 5,695,513 A | | 12/1997 | Johnson et al. |
| 5,810,826 A | | 9/1998 | Akerfeldt et al. |
| 5,843,103 A | * | 12/1998 | Wulfman ........ A61B 17/320758 606/159 |
| 5,871,495 A | * | 2/1999 | Mueller ............. A61B 10/0275 606/167 |
| 6,068,642 A | | 5/2000 | Johnson et al. |
| 6,152,938 A | * | 11/2000 | Curry ............................ 606/159 |

(Continued)

FOREIGN PATENT DOCUMENTS

| | | |
|---|---|---|
| EP | 1542593 B1 | 12/2007 |
| JP | 4496223 B2 | 7/2010 |

*Primary Examiner* — Elizabeth Houston
*Assistant Examiner* — Michael Mendoza
(74) *Attorney, Agent, or Firm* — Price Heneveld LLP

(57) ABSTRACT

A needleless transseptal device assembly, and associated methods, for accessing the left atrium of a human heart includes a tubular body sized to navigate vasculature, and a dilator having a proximal end and a distal end. The dilator is substantially housed and axially movable within the tubular body. The assembly further includes a guidewire that is substantially housed and axially movable within the dilator. The guidewire includes a flexible proximal section and a flexible distal section, and the flexible distal section has a distal end with rotatable, septal tissue cutting elements. The distal end may be configured with a blunt shape. Further, the tubular body and the dilator may be arranged in a steerable configuration. A torquing member may also be coupled to the proximal section of the guidewire to assist in the rotational movement of the septal tissue cutting elements.

14 Claims, 5 Drawing Sheets

(56) References Cited

U.S. PATENT DOCUMENTS

| | | |
|---|---|---|
| 6,312,438 B1 | 11/2001 | Adams |
| 6,650,923 B1 | 11/2003 | Lesh et al. |
| 6,656,195 B2 | 12/2003 | Peters et al. |
| 6,863,529 B2 * | 3/2005 | Strong ............... A61C 8/0089 433/165 |
| 7,048,733 B2 | 5/2006 | Hartley et al. |
| 7,056,294 B2 | 6/2006 | Khairkhahan et al. |
| 7,241,297 B2 | 7/2007 | Shaolian et al. |
| 7,258,694 B1 | 8/2007 | Choi et al. |
| 7,320,695 B2 | 1/2008 | Carroll |
| 7,485,125 B2 | 2/2009 | Sjostrom |
| 7,620,457 B2 | 11/2009 | Ollivier et al. |
| 7,628,763 B2 * | 12/2009 | Noriega ......... A61B 17/320758 600/585 |
| 7,635,353 B2 | 12/2009 | Gurusamy et al. |
| 7,666,203 B2 | 2/2010 | Chanduszko et al. |
| 7,678,081 B2 | 3/2010 | Whiting et al. |
| 7,806,871 B2 | 10/2010 | Li et al. |
| 7,988,704 B2 | 8/2011 | Carroll |
| 8,029,470 B2 | 10/2011 | Whiting et al. |
| 8,114,110 B2 | 2/2012 | Bednarek et al. |
| 8,157,829 B2 | 4/2012 | Chanduszko et al. |
| 8,292,910 B2 | 10/2012 | Chanduszko et al. |
| 2002/0138091 A1 | 9/2002 | Pflueger |
| 2002/0177865 A1 | 11/2002 | McIntosh |
| 2004/0143262 A1 | 7/2004 | Visram et al. |
| 2005/0149097 A1 | 7/2005 | Regnell et al. |
| 2005/0182392 A1 * | 8/2005 | Brucker ................ A61B 18/22 606/15 |
| 2006/0009715 A1 | 1/2006 | Khairkhahan et al. |
| 2006/0079769 A1 | 4/2006 | Whiting et al. |
| 2006/0079787 A1 | 4/2006 | Whiting et al. |
| 2006/0184186 A1 | 8/2006 | Noone |
| 2007/0021739 A1 | 1/2007 | Weber |
| 2007/0083168 A1 | 4/2007 | Whiting et al. |
| 2007/0270741 A1 | 11/2007 | Hassett et al. |
| 2007/0293724 A1 | 12/2007 | Saadat et al. |
| 2008/0103516 A1 | 5/2008 | Wulfman et al. |
| 2008/0214889 A1 | 9/2008 | Saadat et al. |
| 2009/0105654 A1 * | 4/2009 | Kurth ................ A61B 17/3468 604/170.03 |
| 2009/0105742 A1 | 4/2009 | Kurth et al. |
| 2009/0171276 A1 | 7/2009 | Bednarek et al. |
| 2010/0022948 A1 | 1/2010 | Wilson et al. |
| 2010/0106177 A1 | 4/2010 | Chanduszko et al. |
| 2010/0114140 A1 | 5/2010 | Chanduszko et al. |
| 2010/0228276 A1 | 9/2010 | Breznock |
| 2010/0262183 A1 | 10/2010 | Abbott et al. |
| 2011/0054487 A1 | 3/2011 | Farnan |
| 2011/0087261 A1 | 4/2011 | Wittkampf et al. |
| 2011/0264072 A1 | 10/2011 | Kunis |
| 2011/0270191 A1 | 11/2011 | Paul et al. |
| 2011/0270239 A1 | 11/2011 | Werneth |
| 2012/0022564 A1 | 1/2012 | Batten et al. |

\* cited by examiner

NEEDLELESS TRANSSEPTAL ACCESS DEVICE AND METHODS

FIELD OF THE INVENTION

The present invention relates to devices and methods associated with transseptal access to the left atrium in a human heart to facilitate RF ablation, among other cardiac procedures.

BACKGROUND OF THE INVENTION

Transseptal access (i.e., penetration of the septum) is a vital part of many cardiac procedures performed in the left atrium and left ventricle. In general, a catheter is inserted into a vein that runs up to the heart and into the right atrium. The septum is then pierced by a needle assembly within the catheter and the catheter is then advanced into the left atrium. Various imaging techniques, including ultrasound, may be used during the procedure to verify the location of the catheter.

A pathway through the septum is necessary in almost all left atrial catheter ablation procedures for treating atrial fibrillation, left atrial tachycardia and left atrial flutter ablation. Many left ventricular tachycardia ablations also require atrial transseptal access. Further, transseptal access is likely required to deliver newly approved intra-cardiac medical devices such as transcutaneous mitral valves, transcutaneous aortic valves and occluding devices for the left atrial appendage.

SUMMARY OF THE INVENTION

A first aspect of the present invention is to provide a transseptal device assembly that includes a tubular body sized to navigate vasculature. The device assembly further includes a dilator having a proximal end and a distal end. The dilator is substantially housed and axially movable within the tubular body. The device assembly also includes a guidewire substantially housed and axially movable within the dilator. The guidewire has a flexible proximal section and a flexible distal section, wherein the flexible distal section includes a blunt, distal end with rotatable, septal tissue cutting elements.

A second aspect of the present invention is to provide a method for accessing the left atrium of the heart of a patient through the vasculature and the septum of the heart using a transseptal device assembly configured according to the first aspect of the invention. The method includes the steps of advancing the tubular body through the vasculature to a position in proximity to the septum, and advancing the dilator through the vasculature to a position in proximity to the septum. The method also includes the steps of advancing the guidewire within at least one of the tubular body and the dilator to a position such that the blunt, distal end of the flexible distal section is in proximity to the septum, and advancing the guidewire to a position such that the rotatable, septal tissue cutting elements engage the septum. The method further includes the step of rotating the guidewire such that the rotatable, septal tissue cutting elements form a septal access hole in the septum.

A third aspect of the present invention is to provide a method for accessing the left atrium of the heart of a patient through the vasculature and the septum of the heart using a transseptal device assembly configured according to the first aspect of the invention, wherein the flexible distal section of the guidewire is adapted to form a J-shape when the entirety of the flexible distal section is advanced outside of the dilator. The method includes the steps of advancing the tubular body through the vasculature to a position in proximity to the septum, and advancing the dilator through the vasculature to a position in proximity to the septum. The method also includes the steps of advancing the guidewire within at least one of the tubular body and the dilator to a position such that the blunt, distal end of the flexible distal section is in proximity to the septum, and advancing the guidewire to a position such that the rotatable, septal tissue cutting elements engage the septum. The method further includes the steps of rotating the guidewire such that the rotatable, septal tissue cutting elements form a septal access hole in the septum, and advancing the flexible distal section of the guidewire through the septal access hole into the left atrium such that the flexible distal section reverts to the J-shape within the left atrium.

A fourth aspect of the present invention is to provide a transseptal device assembly as follows, including a tubular body sized to navigate vasculature. The device assembly further includes a dilator having a proximal end and a distal end. The dilator is substantially housed and axially movable within the tubular body. The device assembly also includes a guidewire substantially housed and axially movable within the dilator. The guidewire has a flexible proximal section and a flexible distal section, wherein the flexible distal section includes a distal end with rotatable, septal tissue cutting elements. In addition, at least one of the tubular body and the dilator is arranged in a steerable configuration.

A fifth aspect of the present invention is to provide a method for accessing the left atrium of the heart of a patient through the vasculature and the septum of the heart using a transseptal device assembly configured according to the fourth aspect of the present invention. The method includes the steps of advancing the tubular body through the vasculature to a position in proximity to the septum, and advancing the dilator through the vasculature to a position in proximity to the septum. The method also includes the steps of advancing the guidewire within at least one of the tubular body and the dilator to a position such that the distal end of the flexible distal section is in proximity to the septum, and advancing the guidewire to a position such that the rotatable, septal tissue cutting elements engage the septum. The method further includes the step of rotating the guidewire such that the rotatable, septal tissue cutting elements form a septal access hole in the septum.

A sixth aspect of the present invention is to provide a method for accessing the left atrium of the heart of a patient through the vasculature and the septum of the heart using a transseptal device assembly configured according to the fourth aspect of the present invention, wherein the flexible distal section of the guidewire is adapted to form a J-shape when the entirety of the flexible distal section is advanced outside of the dilator. The method includes the steps of advancing the tubular body through the vasculature to a position in proximity to the septum, and advancing the dilator through the vasculature to a position in proximity to the septum. The method also includes the steps of advancing the guidewire within at least one of the tubular body and the dilator to a position such that the distal end of the flexible distal section is in proximity to the septum, and advancing the guidewire to a position such that the rotatable, septal tissue cutting elements engage the septum. The method further includes the steps of rotating the guidewire such that the rotatable, septal tissue cutting elements form a septal access hole in the septum, and advancing the flexible distal section of the guidewire through the septal access hole into the left atrium such that the flexible distal section reverts to the J-shape within the left atrium.

These and other features, advantages, objects, and aspects of the present invention will be further understood and appreciated by those skilled in the art by reference to the following specification, claims, and appended drawings.

DETAILED DESCRIPTION

For purposes of description herein, the terms "upper," "lower," "right," "left," "rear," "front," "vertical," "horizontal," "distal," "proximal," and their derivatives shall relate to the invention as oriented in FIGS. 1A-1E. However, the invention may assume various alternative orientations and step sequences, except where expressly specified to the contrary. Further, the specific devices and processes illustrated in the attached drawings and described in the following specification are exemplary embodiments of the inventive concepts defined in the appended claims. Hence, specific dimensions and other physical characteristics relating to the embodiments disclosed herein are not to be considered as limiting, unless the claims expressly state otherwise.

Transseptal access approaches have significant limitations and some risk. In general, transseptal procedures and associated devices route a catheter with a needle up into the heart and adjacent to the septum. At this point, the needle is advanced longitudinally toward the septum. A longitudinal mechanical force is then applied to the needle to pierce the septum. The needle is sharp and stiff to efficiently puncture the septum. After puncturing the septum, the needle serves as a guidewire to aid in the advancement of other cardiac devices and instruments into the left atrium.

Usually, these approaches produce acceptable results with no danger to the patient. However, a patient's septum may exist in an aneurismal, hypertrophied or fibrosed state. One serious risk associated with these methods is that the needle will pierce the septum, uncontrollably advance through the left atrium, and then pierce a cardiac wall. Particularly when the septum exists in an aneurismal, hypertrophied or fibrosed state, it may stretch when pressed by the advancing needle before it is punctured. Further, it is difficult for the medical practitioner to control the needle during the procedure from outside of the patient's body. In particular, it is challenging to apply the proper axial force to the needle to pierce the septum without further advancement of the needle through the heart. This is the case even though the device and the patient's heart are imaged in real time during the transseptal procedure.

FIGS. 1A through 1E depict a transseptal device assembly 20 for accessing the left atrium of a patient's heart through septal tissue 8 according to an embodiment of the invention. The transseptal device assembly 20 depicted in FIGS. 1A through 1E advantageously reduces the risk of inadvertent, uncontrolled advancement of a guidewire through the left atrium during the transseptal access phase of a subsequent cardiac procedure (e.g., RF ablation). Transseptal access methods associated with the use of device assembly 20, as also depicted in FIGS. 1A through 1E, reduce these risks according to another embodiment of the invention.

Figure 1A:
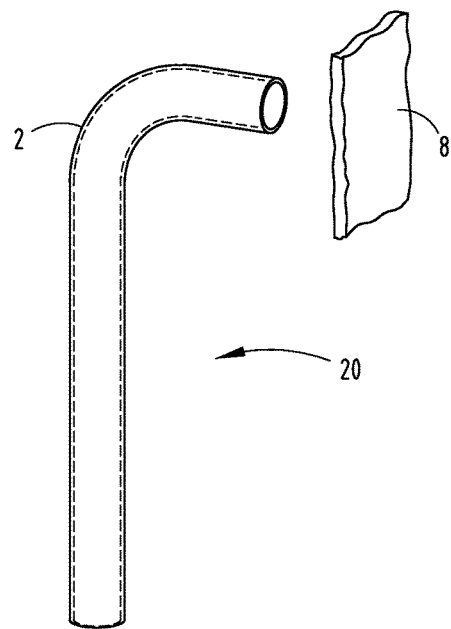
FIG. 1A is a schematic depicting the tubular body of a transseptal device assembly, advanced to a position in proximity to septal tissue of the patient's heart according to one embodiment of the invention.

Referring to FIG. 1A, the transseptal device assembly 20 includes a tubular body 2, sized to navigate the vasculature and heart cavities of a patient (not shown). Tubular body 2 is arranged as a tube-like element, configured with interior walls sufficiently smooth to facilitate movement of other tube- or wire-like elements (see, e.g., FIG. 1B) within tubular body 2. Further, the outer surface of tubular body 2 is adapted to facilitate movement and navigation of tubular body 2 within the vasculature of the patient.

Tubular body 2 should be sufficiently flexible, and appropriately sized in terms of outer diameter, to engage in such movement within the vasculature of the patient. Accordingly, tubular body 2 may be fabricated from various biologically-safe polymeric, metallic and/or composite materials. Tubular body 2, for instance, may be configured as a polyethylene tube-like element, coated with known materials to reduce or minimize the risk of thromboses during the transseptal access procedure.

As shown in FIG. 1A, the tubular body 2 of the device assembly 20 has been routed through the patient's vasculature to a position within the heart in proximity to the septum. The patient's septum is shown schematically as septal tissue 8. Tubular body 2 is typically moved to within a few centimeters of septal tissue 8 during this phase of the transseptal procedure.

Figure 1B:
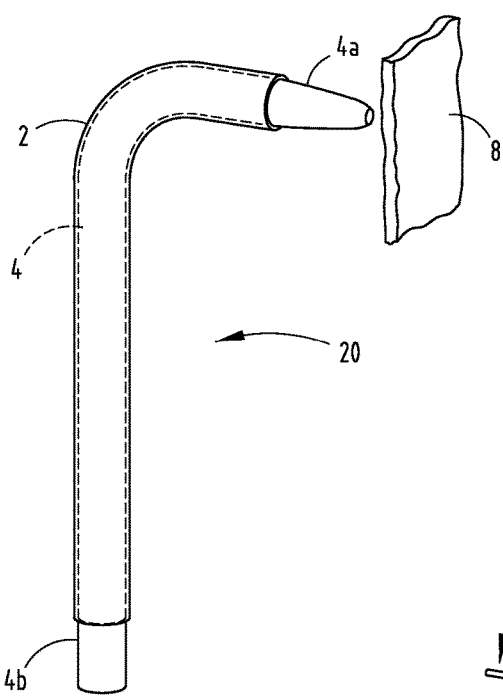
FIG. 1B is a schematic depicting the dilator of the transseptal device assembly shown in FIG. 1A, advanced to a position in proximity to the septal tissue.

Dilator 4 of the transseptal device assembly 20 is shown schematically in FIG. 1B. As shown, dilator 4 is arranged as a tube-like element with distal end 4a and proximal end 4b. Dilator 4 is configured with interior walls sufficiently smooth to facilitate movement of other tube- or wire-like elements (similar to tubular body 2) within dilator 4. The outside surface of dilator 4 is adapted to facilitate movement and navigation of dilator 4 within tubular body 2 and/or vasculature of the patient. Distal end 4a may also be tapered to a diameter slightly larger than the inner diameter of dilator 4 (see, e.g., FIG. 1B). The degree of tapering can be adjusted to improve ease of motion of the dilator 4 within the patient's vasculature and/or tubular body 2. Further, the amount of tapering can be chosen to control the size of the septal access hole 18 created by dilator 4 upon insertion of distal end 4a into the septal access hole 18 initially created by distal end 12 of guidewire 10 (see FIG. 1E).

Like tubular body 2, dilator 4 should be sufficiently flexible, and appropriately sized in terms of outer diameter, to move within the vasculature of the patient and/or tubular body 2 itself. Movement of dilator 4 within the tubular body 2 is generally in an axial direction parallel to the long dimension of tubular body 2 (see FIG. 1B). Accordingly, dilator 4 may be fabricated from various biologically-safe polymeric, metallic, and/or composite materials. For example dilator 4 may be configured as a polyethylene tube-like element, coated with known materials to reduce or minimize the risk of thromboses during the transseptal access procedure.

As also shown in FIG. 1B, the dilator 4 of the device assembly 20 has been routed through the patient's vasculature and tubular body 2 to a position within the heart in proximity to the septum. Further, distal end 4a of dilator 4 is extended past tubular body 2 to a position within the vasculature in close proximity to the septal tissue 8. Dilator 4 is typically moved to within a few centimeters of septal tissue 8 during this phase of the transseptal procedure.

Tubular body 2 and/or dilator 4 are optionally configured with various wires, structures or other known components to impart a steering function or capability for transseptal device assembly 20. When tubular body 2 and/or dilator 4 are arranged in a steerable configuration (not shown), the medical practitioner can more easily direct these elements through the patient's vasculature to the desired position in proximity to the septal tissue 8. Accordingly, a steerable tubular body 2 and dilator 4 can be twisted, bent, turned, etc. to follow the contours of the patient's vasculature. This is a particularly useful feature when the transseptal procedure is conducted during real-time imaging of the patient's heart and associated vasculature. Further, a transseptal device assembly 20 configured with a steerable tubular body 2 and/or dilator 4 can be used to increase the speed of the transseptal access procedure and reduce the risk of damage to the patient's vasculature leading up to the heart.

Figure 1C:
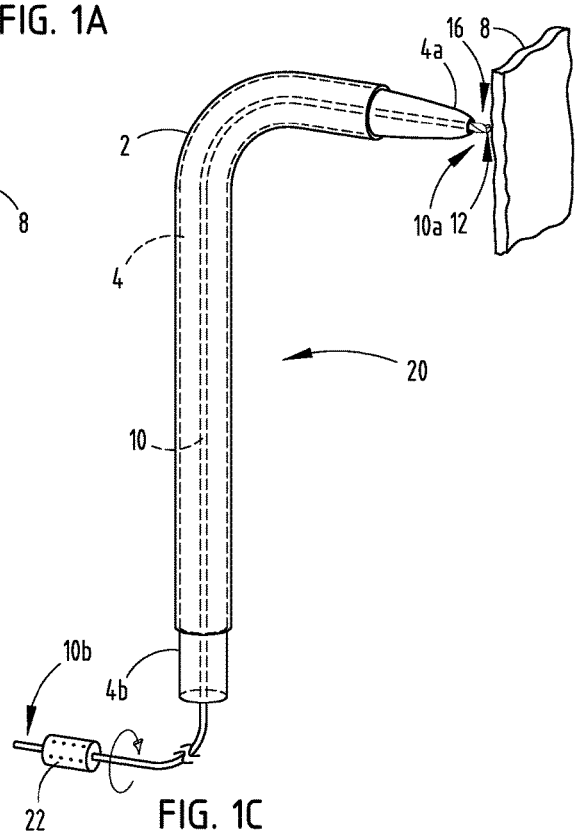
FIG. 1C is a schematic depicting the guidewire of the transseptal device assembly shown in FIG. 1A, advanced to a position such the distal end of the flexible distal section of the guidewire is in proximity to the septal tissue.

FIG. 1C depicts transseptal device assembly 20 in a configuration that includes tubular body 2, dilator 4 and guidewire 10 elements. Guidewire 10 is substantially housed within dilator 4, and configured for axial movement within dilator 4. Further, guidewire 10 includes a flexible distal section 10a and flexible proximal section 10b. Flexible distal section 10a terminates at distal end 12. Distal end 12 includes rotatable, septal tissue cutting elements 16. Proximal section 10b begins at roughly the half-way point along the length of guidewire 10, extending proximally from the distal section 10a.

As depicted in FIG. 1C, the guidewire 10 of transseptal device assembly 20 is routed through dilator 4 to a position within the vasculature of the patient such that the distal end 12 is in proximity to the septal tissue 8. A portion of flexible distal section 10a is advanced past dilator 4. Consequently, distal end 12 is in closer proximity to septal tissue 8 than the distal section 4a of dilator 4. Alternatively, guidewire 10 may be routed directly through tubular body 2 to a similar position in the event that dilator 4 has not yet been introduced within device assembly 20 and the patient's vasculature.

To facilitate advancement and routing of guidewire 10 within dilator 4 or tubular body 2 as shown in FIG. 1C (see also FIGS. 1D and 1E), the distal section 10a and proximal section 10b of guidewire 10 are comprised of materials with appreciable flexibility and/or sized in diameter to promote such flexibility. Appropriate materials should be selected for sections 10a and 10b that provide sufficient flexibility for routing these sections through the curvature of the tubular body 2 and/or dilator 4 to avoid damage to these elements and significant kinking. Further, the materials selected for distal and proximal sections 10a and 10b must have sufficient mechanical strength to minimize the risk of breakage during the procedure. Still further, the selected materials must be biologically-safe, particularly to reduce the risk of formation of thromboses during the transseptal access procedure.

For instance, the flexible distal section 10a and flexible proximal section 10b of guidewire 10 may each comprise a core of material with a modulus of elasticity in the range of approximately 70 to 110 Gigapascals. Further, suitable materials for sections 10a and 10b include titanium alloys, nickel-titanium alloys, and stainless steel alloys. Sections 10a and 10b may be fabricated from the same material, different materials and/or composite materials. In addition, sections 10a and 10b may possess substantially equivalent flexibility, particularly if fabricated from the same material.

As also shown in FIG. 1C, the flexible distal section 10a of guidewire 10 includes a distal end 12. The portion of flexible distal section 10a leading up to distal end 12 may include a degree of taper. This region of distal section 10a includes rotatable, septal tissue cutting elements 16 and, preferably, distal end 12 terminates with a substantially blunt face. The tissue cutting elements 16 for the device assembly 20 shown in FIG. 1C are configured with drill bit-like cutting surfaces. More generally, the rotatable tissue cutting elements 16 are configured to facilitate cutting of septal tissue 8 by the rotational movement of the elements 16 against tissue 8. In addition, septal tissue 8 is subjected to low to negligible amounts of axial force by elements 16 during this cutting step. Accordingly, rotatable, septal tissue cutting elements 16 may be configured with drill bit-like, screw-like, and/or helical cutting surfaces (see FIGS. 2A-4B) to accomplish this function. Other cutting surfaces and/or edges may be configured on the rotatable, septal tissue cutting elements 16 to accomplish this function as well.

The guidewire 10 of the transseptal device assembly 20 depicted in FIG. 1C also may include a torquing member 22. Torquing member 22 is coupled to the flexible proximal section 10b of guidewire 10. In particular, torquing member 22 is adapted to assist in the rotational movement of guidewire 10 and, more particularly, rotational movement of the rotatable, septal tissue cutting elements 16. This rotation is along the long axis of guidewire 10. A medical practitioner, for example, may rotate torquing member 22 in a clockwise or counterclockwise direction, thus imparting rotational movement to the rotatable, septal tissue cutting elements 16 when flexible distal section 10a is situated within the patient's vasculature in close proximity to septal tissue 8.

Figure 1D:
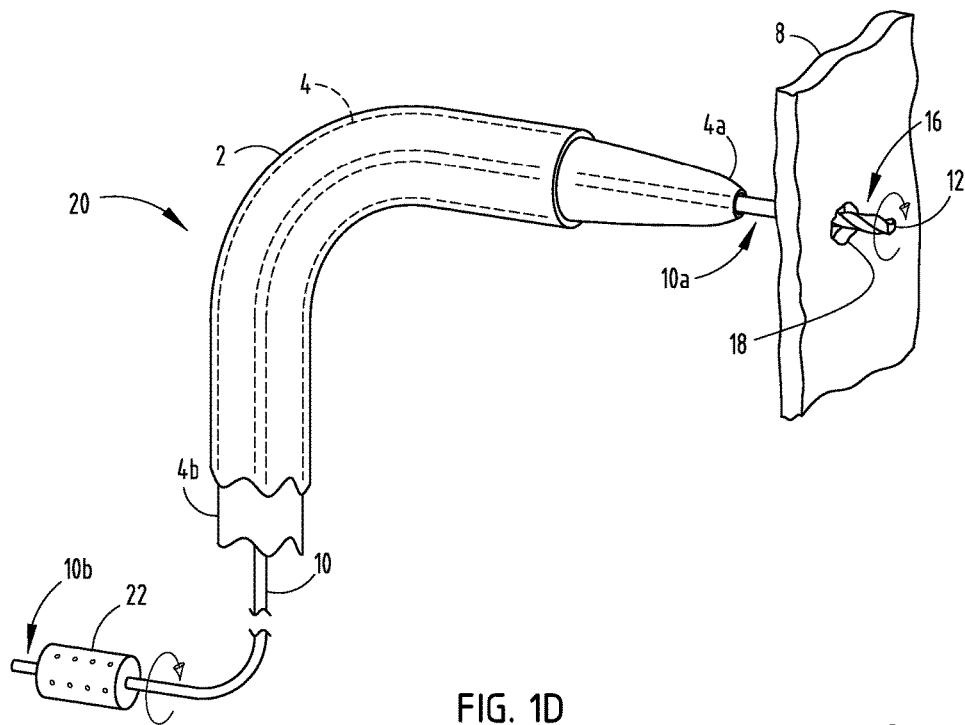
FIG. 1D is a schematic depicting the guidewire of the transseptal device assembly shown in FIG. 1A, advanced to a position such that the rotatable, septal tissue cutting elements of the guidewire engage and cut an access hole in the septal tissue.

In FIG. 1D, the transseptal device assembly 20 is depicted in a configuration adapted to perforate septal tissue 8. Here, the flexible distal section 10a of guidewire 10 has been advanced in the distal direction outside of dilator 4 such that the distal end 12, along with the leading edges of the rotatable, septal tissue cutting elements 16 are placed in contact with septal tissue 8. Despite the flexibility associated with the distal and proximal sections 10a and 10b of guidewire 10, torquing member 22 has been rotated to impart rotation to the tissue cutting elements 16. This rotation of the tissue cutting elements 16 causes the elements to begin cutting septal tissue 8. Cutting continues until septal access hole 18 has been created, allowing the device assembly 20 access from the right atrium to the left atrium.

As shown in FIG. 1D, very little, if any, axial forces applied to guidewire 10 are necessary to cut septal tissue 8 with the transseptal device assembly 20. The rotation of septal tissue cutting elements 16 against septal tissue 8 does the required work. Consequently, there is a minimal risk of inadvertent or uncontrolled axial movement of guidewire 10 through the septal tissue 8 into the patient's left atrium during the procedure. The flexible distal section 10a, and, in particular, the portion of distal section 10a containing tissue cutting elements 16 do not need to possess an added degree of stiffness as device assembly 20 does not rely on a puncture-like action to perforate the septal tissue 8. Rather, the high degree of flexibility associated with flexible distal and proximal sections 10a and 10b makes it easy for the practitioner to position the tissue cutting elements 16 against the septal tissue 8 (as shown in FIG. 1C). But, the guidewire 10 should not kink during the septal tissue cutting step. Once the cutting surfaces (see, e.g., the drill bit-like, screw-like, and helical cutting surfaces 24, 28 and 38 in FIGS. 2A-4B) of the tissue cutting elements 16 are engaged in contact with septal tissue 8, the rotation of these elements should cut the septal tissue 8 without the need to direct the guidewire 10 (and distal section 10a) with much, if any, axial forces against this tissue.

Figure 1E:
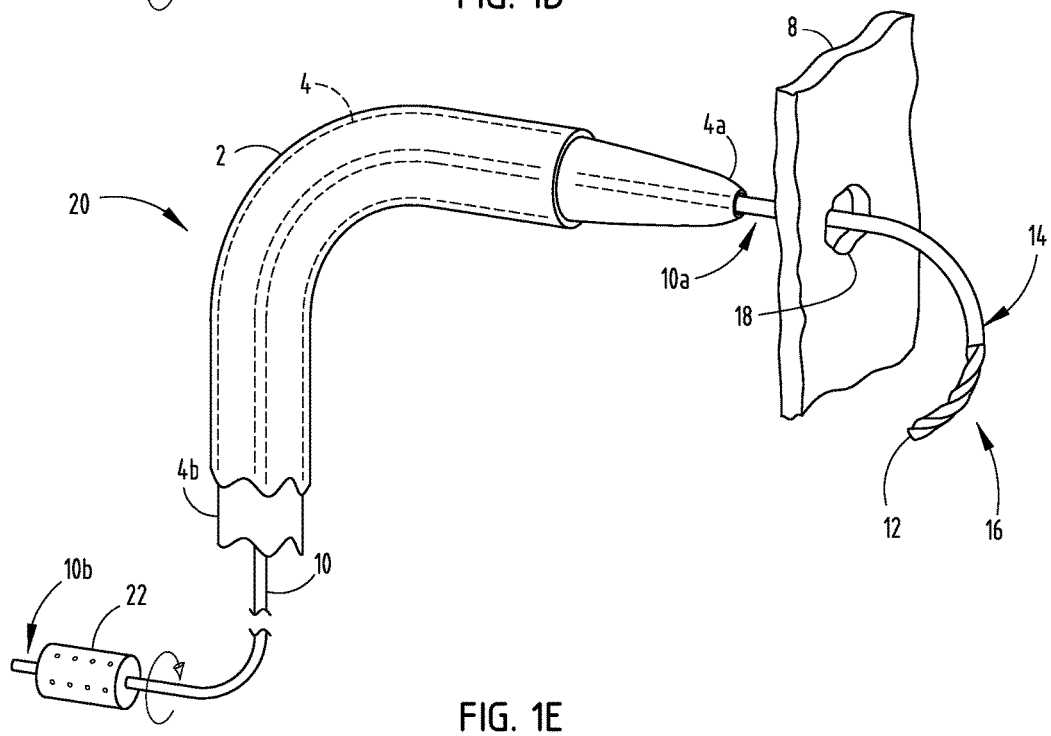
FIG. 1E is a schematic depicting the guidewire of the transseptal device assembly shown in FIG. 1A, configured with a J-shaped bend in the flexible distal section, and advanced through the septal access hole into the left atrium of the patient's heart such that the flexible distal section of the guidewire reverts to the J-shape within the left atrium.

FIG. 1E depicts transseptal device assembly 20 in a configuration in which guidewire 10 has been advanced into the patient's left atrium to facilitate other cardiac procedures (e.g., RF ablation). After septal access hole 18 has been formed in septal tissue 8 by the rotatable, septal tissue cutting elements 16, the flexible distal section 10a of guidewire 10 is advanced further into the patient's left atrium. In the embodiment shown in FIG. 1E, distal section 10a has formed a bend 14 (e.g., a J-shape) after distal section 10a has been advanced through the septal access hole 18. The bend 14 in the flexible distal section 10a is formed when the entirety of the distal section 10a has been advanced outside of the dilator 4. In other words, section 10a forms a bend 14, such as a J-shape, only when guidewire 10 is not constrained by other tubular elements such as dilator 4. This bend 14, optionally configured within flexible distal section 10a, helps to reduce or minimize any inadvertent contact between the distal end 12 and the walls of the patient's left atrium that might lead to damage and/or perforation of the atrial tissue during the transseptal access procedure.

FIGS. 2A through 4B depict embodiments of the rotatable, septal tissue cutting elements 16. As discussed above, tissue cutting elements 16 span a portion of the distal section 10a of guidewire 10 up to the distal end 12 (not shown in FIGS. 2A through 4B). More particularly, the tissue cutting elements 16 are configured with drill bit-like, screw-like, or helical cutting surfaces, as depicted in FIGS. 2A-2B, 3A-3B, and 4A-4B, respectively. When the guidewire 10 is advanced within dilator 4 and/or tubular body 2 (within the patient's vasculature) such that the distal end 12 is in position against septal tissue 8 (see FIG. 1C), the tissue cutting elements 16 can engage septal tissue 8 to cut an access hole 18 (see FIG. 1D). As discussed earlier, guidewire 10 is rotated in a clockwise or counterclockwise direction (e.g., by rotation of the torquing member 22 coupled to proximal section 10b) such that the tissue cutting elements 16 cut the septal tissue 8.

Figure 2A:
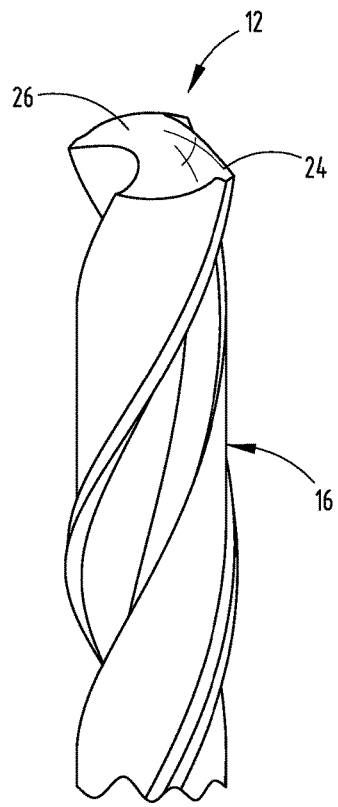
FIG. 2A is an enlarged schematic view of the rotatable, septal tissue cutting elements of the distal section of a guidewire, configured with drill bit-like cutting surfaces according to another embodiment of the invention.
Figure 3A:
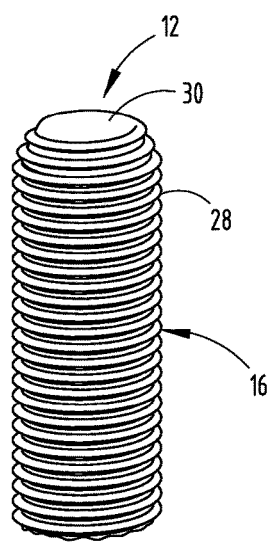
FIG. 3A is an enlarged schematic view of the rotatable, septal tissue cutting elements of the distal section of a guidewire, configured with screw-like cutting surfaces according to another embodiment of the invention.
Figure 4A:
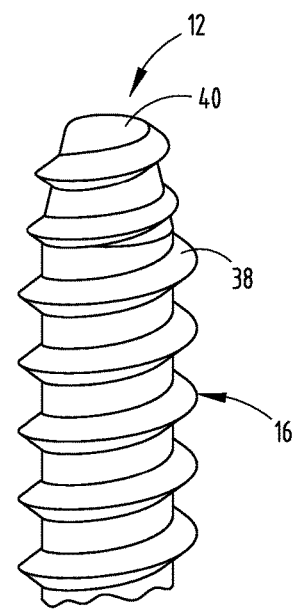
FIG. 4A is an enlarged schematic view of the rotatable, septal tissue cutting elements of the distal section of a guidewire, configured with helical cutting surfaces according to another embodiment of the invention.
Figure 2B:
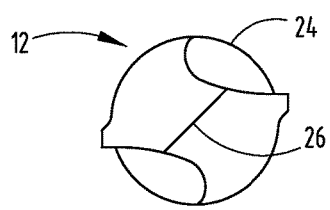
FIG. 2B is a top-down view of the rotatable, septal tissue cutting elements configured with drill bit-like cutting surfaces depicted in FIG. 2A.
Figure 3B:
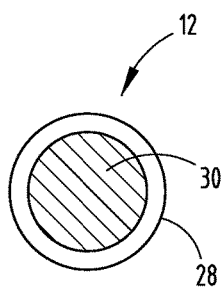
FIG. 3B is a top-down view of the rotatable, septal tissue cutting elements configured with screw-like cutting surfaces depicted in FIG. 3A.
Figure 4B:
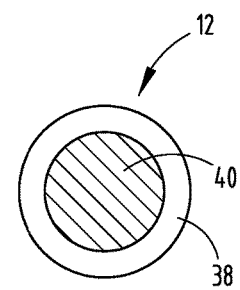
FIG. 4B is a top-down view of the rotatable, septal tissue cutting elements configured with helical cutting surfaces depicted in FIG. 4A.

FIGS. 2A and 2B, in particular, depict septal tissue cutting elements 16 with drill bit-like cutting surfaces 24 and a blunt end 26. FIGS. 3A and 3B depict septal tissue cutting elements 16 with screw-like cutting surfaces 28 and a blunt end 30. FIGS. 4A and 4B depict septal tissue cutting elements 16 with helical cutting surfaces 38 and a blunt end 40.

The pitch, sharpness, angle relative to the longitudinal axis of the guidewire 10, and other shape aspects of the cutting surfaces 24, 28, and 38 may be adjusted to affect the degree of septal tissue cutting as a function of guidewire rotational movement, smoothness of the cut, manufacturability, and other aspects of the transseptal access procedure. In addition, these characteristics associated with cutting surfaces 24, 28, and 38 may be optimized to accommodate certain septal tissue morphologies—e.g., fibrosed, hypertrophied, and aneurismal—during the transseptal access procedure.

The blunt ends 26, 30 and 40 of the drill bit-like, screw-like and helical cutting surfaces 24, 28 and 38 of the tissue cutting elements 16 depicted in FIGS. 2A-2B, 3A-3B and 4A-4B, respectively, provide additional safety margin. In particular, these blunt end features provide further assurance that the distal section 10a does not uncontrollably or inadvertently enter the left atrium of the patient's heart during the cutting step of the transseptal access procedure. Even if a practitioner applies significant axial force from guidewire 10, distal section 10a and distal end 12 against septal tissue 8, these blunt end features 26, 30 and 40 help ensure that the septal tissue 8 is not pierced or perforated by this action. When the tissue cutting elements 16 are configured with blunt ends 24, 38 and 40 as depicted in FIGS. 2A-4B, the transseptal device assembly 20 can only be effectively used by a medical practitioner to access the left atrium by rotational movement of guidewire 10 and flexible distal section 10a to cut septal tissue 8. In other words, the assembly 20, arranged in this fashion, is more of a fail-safe device, virtually incapable of uncontrolled perforation of the septum.

FIGS. 5A through 5E depict a method for accessing the left atrium of a patient's heart using the transseptal device assembly 20 (depicted schematically in FIGS. 1A through 1E) according to a further embodiment. FIGS. 5A through 5E parallel FIGS. 1A through 1E that schematically depict the use of transseptal device assembly 20 to access the left atrium 56 of a patient's heart 50. As shown in FIGS. 5A through 5E, the patient's heart 50 includes a right ventricle 52, left ventricle 54, right atrium 58, septum 60 and inferior vena cava 62. Each of the views depicted in FIGS. 5A through 5E are cross-sections of the heart. For purposes of clarity, the vena cava and aorta are not shown in these views.

Figure 5A:
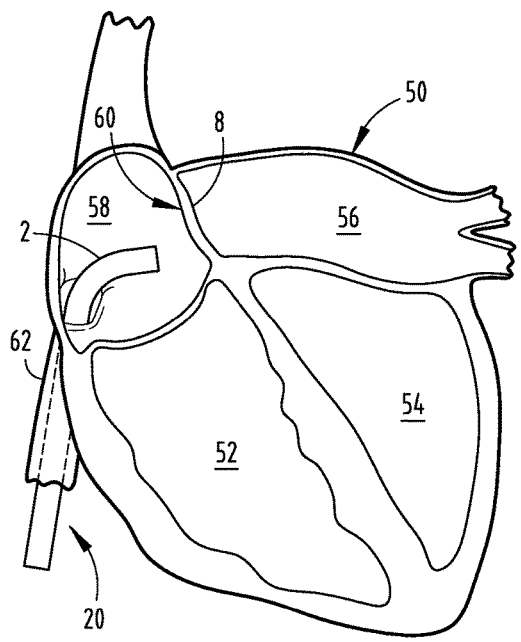
FIG. 5A is a schematic depicting the advancement of the tubular body of a transseptal device assembly through the vasculature of a patient to a position in the patient's heart in proximity to the septum according to an embodiment of the invention.

FIG. 5A depicts the step of advancing the tubular body 2 through the vasculature of the patient, e.g., inferior vena cava 62 and right atrium 58, to a position in proximity to the septum 60 and, more particularly, septal tissue 8. Generally, tubular body 2 is advanced to within a few centimeters of septal tissue 8 during this step of the transseptal access procedure.

Figure 5B:
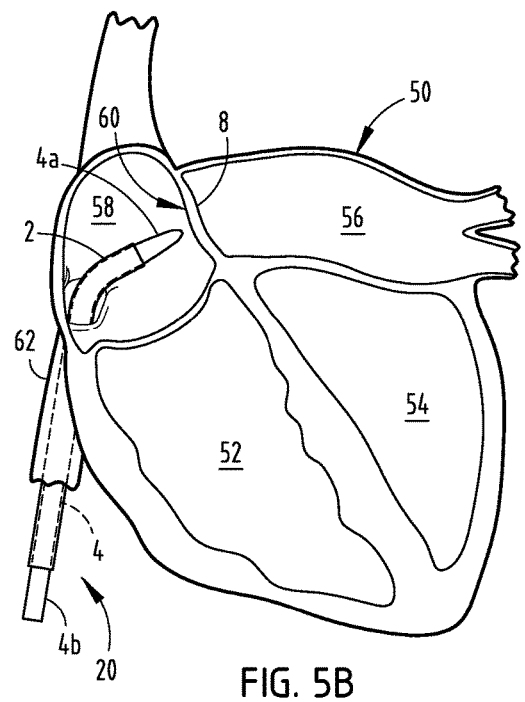
FIG. 5B is a schematic depicting the advancement of the dilator of the transseptal device assembly shown in FIG. 5A to a position in the patient's heart in proximity to the septum.

As shown in FIG. 5B, dilator 4 can be advanced through the vasculature of the patient, e.g., inferior vena cava 62 and right atrium 58, to a position in proximity to the septum 60 and septal tissue 8. Further, distal end 4a of dilator 4 is extended past tubular body 2 to within a few centimeters of septal tissue 8 during this step.

Figure 5C:
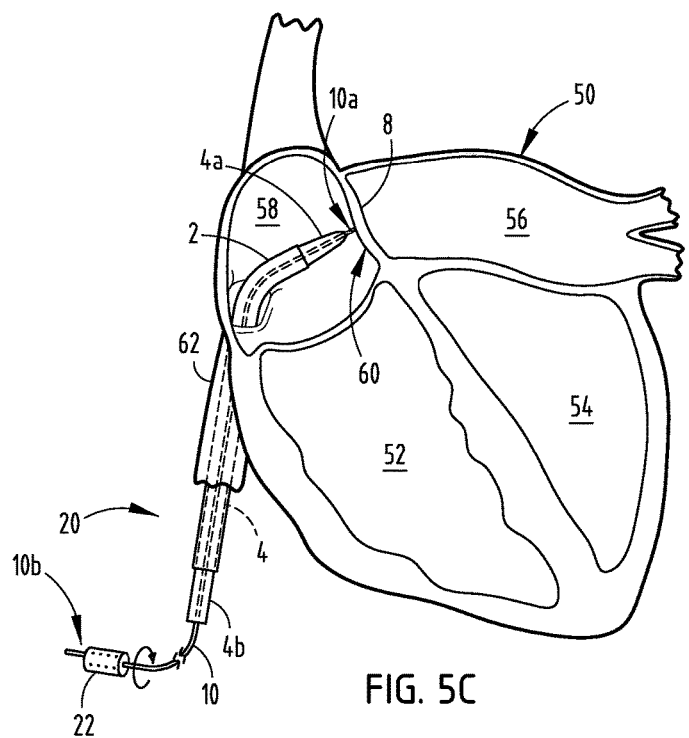
FIG. 5C is a schematic depicting the advancement of the guidewire of the transseptal device assembly shown in FIG. 5A to a position in the patient's heart such the distal end of the flexible distal section of the guidewire is in proximity to the septum.

In FIG. 5C, guidewire 10 is advanced through dilator 4 to a position within the vasculature of the patient, e.g., inferior vena cava 62 and the right atrium 58, such that a portion of flexible distal section 10a extends past the distal section 4a of dilator 4. Flexible distal section 10a terminates in distal end 12 (not shown). Hence, distal end 12 is located in close proximity to septum 60 and, more particularly, septal tissue 8 during this step. Alternatively, guidewire 10 and flexible distal section 10a may be advanced directly through tubular body 2 to the same approximate position relative to septum 60 and septal tissue 8, provided that the dilator 4 has not yet been introduced within transseptal device assembly 20 during the procedure.

Figure 5D:
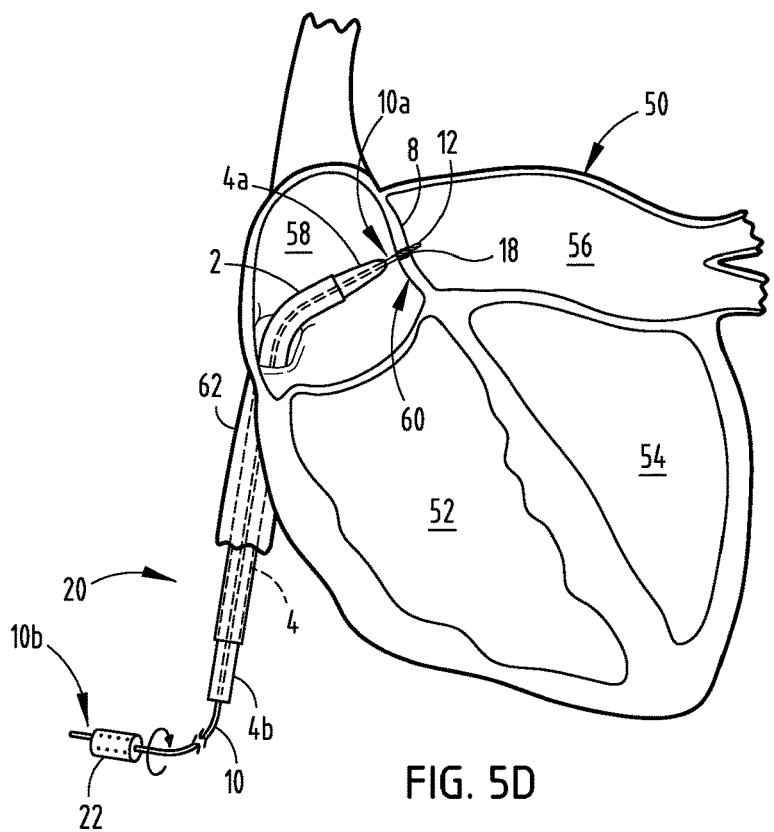
FIG. 5D is a schematic depicting the further advancement of the guidewire of the transseptal device assembly shown in FIG. 5A such that the rotatable, septal tissue cutting elements of the guidewire engage and cut an access hole in the septum, and the flexible distal section has advanced through the access hole into the left atrium.

In FIGS. 5C and 5D, distal section 10a of guidewire 10 is advanced in the right atrium 58 and further extended outside of distal section 4a of dilator 4 such that the distal end 12 of guidewire 10 is placed in contact with septum 60 and septal tissue 8. Accordingly, septal tissue cutting elements 16, arranged along flexible distal section 10a, are placed in contact with septum 60 and septal tissue 8. As shown in FIG. 5D, guidewire 10, distal section 10a and the rotatable, septal tissue cutting elements 16 are rotated to engage the cutting surfaces of the cutting elements 16 with septal tissue 8. As the cutting surfaces of the cutting elements 16 are rotated against septal tissue 8, the septal tissue 8 is cut and an access hole 18 is created from the right atrium 58 to the left atrium 56. The rotation of septal tissue cutting elements 16 does the required work to cut the access hole 18 in the septal tissue 8. Consequently, there is a low risk of inadvertent or uncontrolled axial movement of guidewire 10 into the left atrium 56. In addition, the optional use of a blunt end (e.g., blunt ends 24, 30 and 40 shown in FIGS. 2A, 3A and 4A) on distal end 12 further reduces the risk of inadvertent or uncontrolled axial movement of guidewire 10 and distal section 10a into the left atrium 56.

As also shown in FIG. 5D, guidewire 10, distal section 10a and the tissue cutting elements 16 can be rotated by the medical practitioner through rotational motion of the torquing member 22. Torquing member 22 is coupled to the proximal section 10b of the guidewire 10. Other modifications can be made to the proximal section 10b that aid in the generation of the rotational motion necessary to create septal access hole 18. In addition, the practitioner can employ other techniques and devices to effect this rotation (e.g., the use of a low-speed drill attached to proximal section 10b).

Figure 5E:
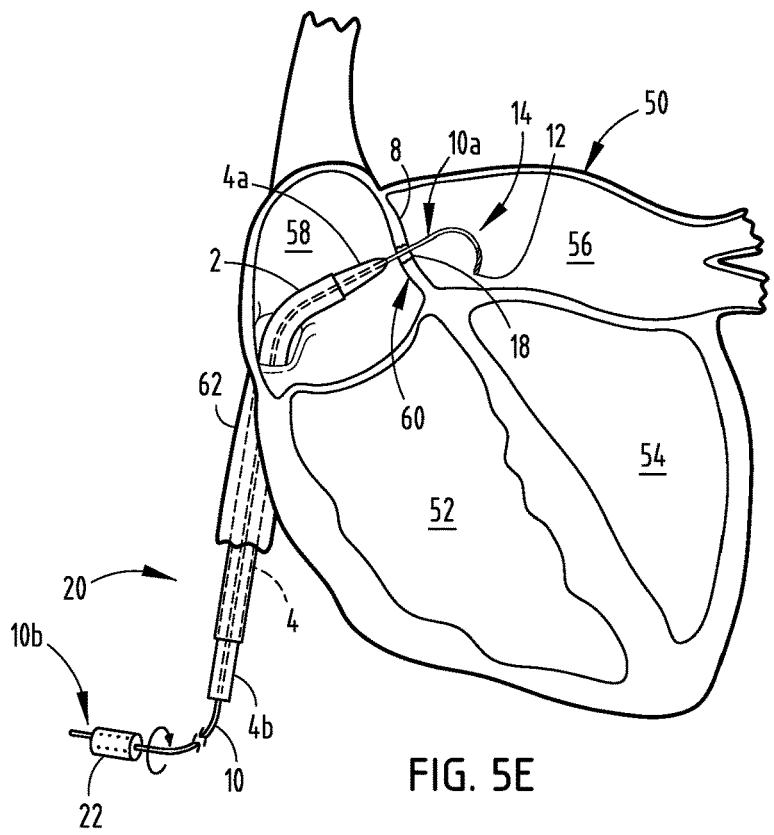
FIG. 5E is a schematic depicting additional advancement of the guidewire of the transseptal device assembly shown in FIG. 5A, configured with a J-shaped bend in the flexible distal section, to a position in the patient's heart through the septal access hole and into the left atrium such that the flexible distal section of the guidewire reverts to the J-shape within the left atrium.

In FIG. 5E, transseptal device assembly 20 is shown in a configuration in which guidewire 10 has been further advanced into the left atrium 56, setting the stage for other cardiac procedures within the heart (e.g., RF ablation, installation of cardiac devices, valve repair, etc.). After the formation of the septal access hole 18 in the step depicted in FIG. 5D, the septal tissue cutting elements 16 and distal section 10a of the guidewire 10 are positioned further within left atrium 16. Distal section 10a includes a bend 14 that forms when the entirety of the distal section 10a has been advanced outside of dilator 4 and into left atrium 56. As such, bend 14 (when guidewire 10 is configured with this feature) only forms when distal section 10a is not constrained by other tubular elements housing the guidewire 10, e.g., dilator 4 and/or tubular body 2. Bend 14 minimizes inadvertent contact between distal end 12 and the walls of the left atrium 56 during the transseptal access procedure.

After distal section 10a has been fully advanced into the left atrium as shown in FIG. 5E, the practitioner can increase the size of septal access hole 18 by the insertion of dilator 4 (this step not shown). A larger septal access hole 18 allows for the introduction of other larger diameter medical devices into the left atrium 56. In particular, the larger diameter of access hole 18 facilitates other cardiac procedures within the left atrium 56, e.g., left atrial valve repair (not shown).

Variations and modifications can be made on the aforementioned structure without departing from the concepts of the present invention. Such modifications are to be considered within the scope of the following claims, unless these claims by their language expressly state otherwise. Accordingly, the scope of the invention should be considered in terms of the following appended claims and is understood not to be limited to the details of the structure and operation shown and described in the foregoing specification and drawings.

We claim:

1. A needleless transseptal device assembly, comprising:
 a tubular body with an outer diameter sized to navigate human vasculature;
 a dilator comprising a proximal end and a distal end, the dilator substantially housed and axially movable within the tubular body; and
 a guidewire having an outer diameter that is substantially housed and axially movable within the dilator, the guidewire comprising a flexible proximal section and a flexible distal section that comprises an end surface region having rotatable, needleless septal tissue cutting elements and a blunt, substantially planar distal end surface normal to the primary axis of the guidewire,
 wherein the distal section is configured to initiate, and complete, cutting of septal tissue to form a septal access hole with a diameter substantially equivalent to the outer diameter of the guidewire,
 wherein the rotatable, septal tissue cutting elements comprise at least one of drill bit-like, screw-like and helical cutting surfaces for cutting sepal tissue by a rotation action, and further wherein the distal section of the guidewire forms a j-shape only when the entirety of the distal section is advanced outside of the dilator past the septal access hole into a heart atrium.

2. The device assembly according to claim 1, wherein the flexible proximal section and the flexible distal section of the guidewire each comprise a core of substantially the same material.

3. The device assembly according to claim 1, wherein the flexible proximal section and the flexible distal section of the guidewire each possess substantially equivalent flexibility.

4. The device assembly according to claim 1, wherein the flexible proximal section and the flexible distal section of the guidewire each comprise a core of material selected from the group consisting of titanium alloys, nickel-titanium alloys and stainless steel alloys.

5. The device assembly according to claim 1, wherein the flexible proximal section and the flexible distal section of the guidewire each comprise a core of material with a modulus of elasticity in the range of approximately 70 to 110 Gigapascals.

6. The device assembly according to claim 1, further comprising:
a torquing member coupled to the flexible proximal section of the guidewire, wherein the torquing member is adapted to assist in a rotational movement of the rotatable, septal tissue cutting elements to cut septal tissue.

7. The device assembly according to claim 1, wherein the dilator further comprises a tapered end adapted to widen the septal access hole.

8. A needleless transseptal device assembly, comprising:
a tubular body with an outer diameter sized to navigate human vasculature;
a dilator comprising a proximal end and a distal end, the dilator substantially housed and axially movable within the tubular body; and
a guidewire having an outer diameter that is substantially housed and axially movable within the dilator, the guidewire comprising a flexible proximal section and a flexible distal section that comprises an end surface region having rotatable, needleless septal tissue cutting elements and a blunt, substantially planar distal end surface normal to the primary axis of the guidewire,
wherein the distal section is configured to initiate, and complete, cutting of septal tissue to form a septal access hole with a diameter substantially equivalent to the outer diameter of the guidewire,
wherein the rotatable, septal tissue cutting elements comprise at least one of drill bit-like, screw-like and helical cutting surfaces for cutting septal tissue by a rotational action,
further wherein the distal section of the guidewire forms a j-shape only when the entirety of the distal section is advanced outside of the dilator past the septal access hole into a heart atrium, and
further wherein at least one of the tubular body and the dilator further comprises a wire that allows a medical practitioner to steer the at least one of the tubular body and the dilator within the vasculature.

9. The device assembly according to claim 8, wherein the flexible proximal section and the flexible distal section of the guidewire each comprise a core of substantially the same material.

10. The device assembly according to claim 8, wherein the flexible proximal section and the flexible distal section of the guidewire each possess substantially equivalent flexibility.

11. The device assembly according to claim 8, wherein the flexible proximal section and the flexible distal section of the guidewire each comprise a core of material selected from the group consisting of nickel-titanium alloys and stainless steel alloys.

12. The device assembly according to claim 8, wherein the flexible proximal section and the flexible distal section of the guidewire each comprise a core of material with a modulus of elasticity in the range of approximately 70 to 110 Gigapascals.

13. The device assembly according to claim 8, further comprising:
a torquing member coupled to the flexible proximal section of the guidewire, wherein the torquing member is adapted to assist in a rotational movement of the rotatable, septal tissue cutting elements to cut septal tissue.

14. The device assembly according to claim 8, wherein the dilator further comprises a tapered end adapted to widen the septal access hole.

* * * * *

UNITED STATES PATENT AND TRADEMARK OFFICE
CERTIFICATE OF CORRECTION

| | | |
|---|---|---|
| PATENT NO. | : 10,179,009 B2 | Page 1 of 1 |
| APPLICATION NO. | : 13/568504 | |
| DATED | : January 15, 2019 | |
| INVENTOR(S) | : Abdul-Karim | |

It is certified that error appears in the above-identified patent and that said Letters Patent is hereby corrected as shown below:

In the Claims

Column 10, Claim 1, Line 66:
"rotation" should be -- rotational --.

Column 11, Claim 1, Line 2:
"j-shape" should be -- J-shape --.

Column 12, Claim 8, Line 10:
"j-shape" should be -- J-shape --.

Signed and Sealed this
Eighteenth Day of June, 2019

Andrei Iancu
*Director of the United States Patent and Trademark Office*